United States Patent [19]
Buckle et al.

[11] 4,059,704
[45] Nov. 22, 1977

[54] TETRAZOLE COUMARIN DERIVATIVES

[75] Inventors: Derek Richard Buckle, Redhill; Barrie Christian Charles Cantello, Horsham; Harry Smith, Maplehurst, near Horsham, all of England

[73] Assignee: Beecham Group Limited, Great Britain

[21] Appl. No.: 672,753

[22] Filed: Apr. 1, 1976

Related U.S. Application Data

[62] Division of Ser. No. 508,749, Sept. 24, 1974, abandoned.

[30] Foreign Application Priority Data

Oct. 11, 1973 United Kingdom ............... 47484/73

[51] Int. Cl.² .................... A61K 31/41; C07D 257/04

[52] U.S. Cl. ................................ 424/269; 260/308 D
[58] Field of Search .................... 424/269; 260/308 D

[56] References Cited

FOREIGN PATENT DOCUMENTS 2,105,191   2/1971   Germany

OTHER PUBLICATIONS

J. C. S., Perkins, 1, 779–783, (1972).

*Primary Examiner*—Frederick E. Waddell
*Attorney, Agent, or Firm*—Jacobs & Jacobs

[57] ABSTRACT

A novel class of 3-tetrazole coumarins have anti-allergic activity. They are prepared by the action of ammonium azide on 3-cyano compounds.

27 Claims, No Drawings

TETRAZOLE COUMARIN DERIVATIVES

This is a division of Ser. 508,749 filed Sept. 24, 1974, now abandoned.

This invention relates to compounds which are useful in the inhibition of the effects of certain types of antigen-antibody reactions and are therefore useful in the prophylaxis and treatment of diseases associated with allergic or immunological reactions, e.g. certain types of asthma and hay-fever, and also in the treatment of rhinitis. The invention also relates to the preparation of such compounds and to pharmaceutical compositions comprising them.

According to the present invention there is provided a class of compounds of formula (I):

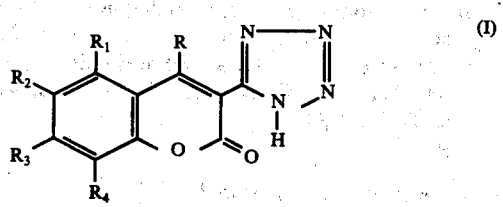

and pharmaceutically acceptable salts thereof wherein R is an alkyl or aryl group; $R_1$, $R_2$, $R_3$ and $R_4$ are independently hydrogen or alkyl, alkoxy, aryl, aralkyl, heterocyclic, halogen, carboxylic acid groups or pharmaceutically acceptable salt, ester or amide derivatives of carboxylic acid groups or acyloxy groups, or any two of $R_1$, $R_2$, $R_3$ and $R_4$ taken together represent the residue of a substituted or unsubstituted carbocyclic or heterocyclic group; the foregoing definition of the various groups R, $R_1$, $R_2$, $R_3$ and $R_4$ being subject to the proviso that when $R_1 = R_2 = R_3 = R_4 = H$, R is not methyl.

The above definition of the compounds of this invention excludes 4-methyl-3-(tetrazol-5-yl) coumarin since this compound is already known from the literature (J.Chem.Soc. Perkin Trans I, 779, 1972). Further, in that paper the authors conclude that the compound has no anti-allergic activity. Surprisingly, we have found that in our hands the compound exhibits substantial antiallergic activity, and our preliminary results encourage us to believe that the compounds of formula (I) above also are active anti-allergic agents.

The group R in components (I) is an alkyl or aryl group. Examples of suitable alkyl or aryl groups include methyl ethyl, n- and iso- propyl, n-, sec- or tert butyl, cyclohexyl, cyclopentyl, cycloheptyl and phenyl groups. A lower alkyl group is preferred, in particular the methyl group.

Examples of the groups $R_1$, $R_2$, $R_3$ and $R_4$ which may be present in the compounds of this invention include hydrogen methyl, ethyl, n- and iso- propyl, n-, sec- and tert- butyl, cyclohexyl, methoxy, ethoxy, n- and isopropoxy, n-, sec- and tert-butoxy; phenyl; benzyl; pyridyl and tetrazolyl; fluoro, chloro, bromo and iodo; carboxyl, alkoxycarbonyl, acyloxymethoxycarbonyl, -acyloxyethoxycarbonyl and acetoxy groups. In addition any two adjacent groups $R_1$ and $R_2$, $R_2$ and $R_3$, $R_3$ and $R_4$ taken together may represent the residue of a 1,2-phenylene or 1,2 - cyclohexylene ring.

Preferred sub-groups of compounds of formula (I) include those wherein:
a. $R_4$ is halogen;
b. $R_2$ is lower alkyl, especially methyl c. $R_2$ and $R_3$ are both lower alkyl, especially methyl; and
d. $R_3$ is lower alkoxy.

Examples of specific compounds of this invention include the following, and their pharmaceutically acceptable salts:-

6-Bromo-4-Methyl-3-(tetrazol-5-yl) coumarin;
6-Chloro-4-Methyl-3-(tetrazol-5-yl) coumarin;
3-(Tetrazol-5-yl)-4,6,7-trimethyl coumarin;
6-Bromo-4-Ethyl-3-(tetrazol-5-yl) coumarin;
8-Chloro-4-methyl-3-(tetrazol-5-yl) coumarin;
4-Ethyl-3-(tetrazol-5-yl) coumarin;
4-Methyl-8-nitro-3-(tetrazol-5-yl) coumarin;
6-methoxy-4-methyl-3-(tetrazol-5-yl) coumarin;
6,8-dichloro-4-methyl-3-(tetrazol-5-yl) coumarin;
4,6,8-Trimethyl-3-(tetrazol-5-yl) coumarin;
4-n-Propyl-3-(tetrazol-5-yl) coumarin;
4,6-dimethyl-3-(tetrazol-5-yl) coumarin;
4,7-dimethyl-3-(tetrazol-5-yl) coumarin;
7,8-benzo-4-methyl-3-(tetrazol-5-yl) coumarin;
4-phenyl-3-(tetrazol-5-yl) coumarin;
6,7-diethyl-4-methyl-3-(tetrazol-5-yl) coumarin;
4,6,7-trimethyl-3-(tetrazol-5-yl) coumarin;
8-bromo-4-methyl-3-(tetrazol-5-yl) coumarin;
7-methoxy-4-methyl-3-(tetrazol-5-yl) coumarin.

Suitable pharmaceutically acceptable salts of compounds (I) include non-toxic metal salts such as sodium, potassium, aluminium or calcium salts.

The present invention also provides pharmaceutical compositions comprising one or more pharmaceutically acceptable carriers and a compound of formula (I) or a pharmaceutically acceptable salt thereof:

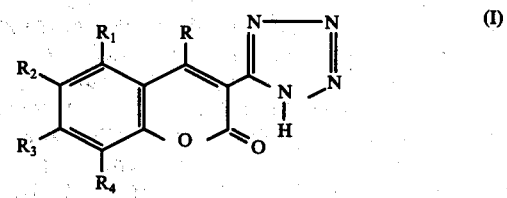

wherein R is an alkyl or aryl group; $R_1$, $R_2$, $R_3$ and $R_4$ are independently hydrogen or alkyl, alkoxy, aryl, aralkyl, heterocyclic, halogen, carboxylic acid groups or pharmaceutically acceptable salt, ester or amide derivatives of carboxylic acid groups, or acyloxy groups, or any two of $R_1$, $R_2$, $R_3$ and $R_4$ taken together represent the residue of a substituted or unsubstituted carbocyclic or heterocyclic group; the foregoing definition of the various groups R, $R_1$, $R_2$, $R_3$, and $R_4$ being subject to the proviso that when $R_1 = R_2 = R_3 = R_4 = H$, R is not methyl.

The compositions of this invention may be presented as a microfine powder for insufflation, e.g. as a snuff or in capsules or hard gelatin. They may also be presented together with a sterile liquid carrier for injection. Some of the compounds of formula (I) are active when given by the oral route and in such cases the compositions of the invention may be in the form of tablets, capsules, pills, or syrups. Preferably the compositions of this invention are presented in unit dosage form, or in a form in which the patient can administer to himself a single dose. If desired, a small amount of a bronchodilator compound such as isoprenaline may be incorporated in the compositions both to inhibit the cough response of the composition is insufflated and to provide immediate relief during an asthmatic attack. The effective dose of compound (I) depends on the particular compound chosen, but is generally in the range of from 0.1 mg/kg/day to 100 mg/kg/day.

The precise identity of the pharmaceutical carrier is not important and standard pharmaceutical practice may be followed.

In another special aspect of this invention there is provided a pharmaceutical composition comprising 4-methyl-3-(tetrazol-5-yl) coumarin or a pharmaceutically acceptable salt thereof, together with one or more solid, pharmaceutically acceptable carriers. Suitable carriers include gelatin capsules, lactose, mannitol and the like.

Compounds of this invention may be prepared by a process which comprises reacting the appropriate 3-cyano coumarin with ammonium azide. Preferably the reaction is carried out in an inert organic solvent such as dimethylformamide at a temperature above room temperature. Preferably also the ammonium azide is formed in situ, e.g. by the reaction of sodium azide with ammonium chloride.

Example 1 which follows illustrates the preparation of the known compound 4-methyl-3-(tetrazol-5-yl) coumarin, and is included since the biological activity of the compound is confirmed below. Examples 2–11 illustrate the preparation of some of the compounds of the invention.

EXAMPLE 1

4-Methyl-3-(tetrazol-5-yl) coumarin

A solution of 3-cyano-4-methyl coumarin (7.94 g; 0.043 mole) in cimethylformamide (DMF) (45 ml) was added to a mixture of sodium azide (2.92 g; 0.044 mole) and ammonium chloride (2.36 g; 0.044 mole) and the stirred mixture heated on a steam bath for 24 hours. After removal of the solvent under reduced pressure, water (100 ml) was added and the solid filtered off. Acidification of the filtrate, and further aqueous extracts, afforded the title compound; m.p. (EtOH) 213°–4° C (Found: C, 57.58; H, 3.51; N, 24.41; $C_{11}H_8N_4O_2$ requires; C, 57.89; H, 3.53; N, 24.55%).

EXAMPLE 2

6-Bromo-4-methyl-3-(tetrazol-5-yl) coumarin

Similar treatment of 6-bromo-3-cyano-4-methyl coumarin (m.p. 187°–192° C) gave the tetrazolyl compound, m.p. (EtOH) 238°–9° C. (Found: C, 43.02; H, 2.30; N, 18.24; $C_{11}H_7BrN_4O_2$ requires; C, 43.27; H, 2.50; N, 18.38%).

EXAMPLE 3

6-Chloro-4-methyl-3-(tetrazol-5-yl) coumarin

The reaction of 6-Chloro-3-cyano-4-methyl coumarin with ammonium azide as described in Example 1 yielded the title product, m.p. (EtOH) 219°–223° C. (Found: C, 50.30; H, 2.69; N, 21.33; $C_{11}H_7ClN_4O_2$ requires; C, 50.04; H, 2.84; N, 21.63%).

EXAMPLE 4

3-(Tetrazol-5-yl)-4,6,7-trimethyl coumarin

Reaction of 3-cyano-4,6,7-trimethyl coumarin (m.p. 193° C) with ammonium azide as described in Example 1 gave the 3-tetrazolyl derivative, m.p. (EtOH) 226°–228° C (Found: C, 60.93; H, 4.72; N, 21.86; $C_{13}H_{12}N_4O_2$ requires C, 60.75; H, 4.85; N, 21.87%).

EXAMPLE 5

4,6-Dimethyl-3-(tetrazol-5-yl) coumarin

To a solution of 3-cyano-4,6-dimethyl coumarin (16.43 g, 0.083 mole) in DMF (88 ml) was added sodium azide (5.69 g) and ammonium chloride (4.60 g). After stirring at 100° C for 29 hours the cooled mixture was stripped of solvent under reduced pressure and the residual solid extracted with water. Acidification of the extracts gave the tetrazolyl derivative as a white solid, m.p. (EtOH) 206°–209° C (Found; C, 59.25; H, 4.46; N, 22.86; $C_{12}H_{10}N_4O_2$ requires; C, 59.50; H, 4.16; N, 23.13%).

EXAMPLE 6

4,7-Dimethyl-3-(tetrazol-5-yl) coumarin

By an analogous procedure to that used in Example 5, 3-cyano 4,7-dimethyl coumarin (22.71 g; 0.114 mole) was converted into its tetrazolyl derivative. It had m.p. (EtOH) 211°–214° C. (Found; C, 59.72; H, 4151; N, 23.15; $C_{12}H_{10}N_4O_2$ requires; C, 59.50; H, 4.16; N, 23.13%).

EXAMPLE 7

8-Chloro-4-methyl-3-(tetrazol-5-yl) coumarin

The reaction of ammonium azide on 8-chloro-3-cyano-4-methyl coumarin as described in Example 1 afforded the title product, m.p. (EtOH) 230°–232° C (Found; C, 50.23; H, 3.05; N, 21.55; Cl, 13.22; $C_{11}H_7ClN_4O_2$ requires; C, 50.30; H, 2.69; N, 21.33; Cl, 13.50%).

EXAMPLE 8

7,8-Benzo-4-methyl-3-(tetrazol-5-yl) coumarin

Reaction of 7,8-benzo-3-cyano-4-methyl coumarin (20 g; 0.107 mole) with ammonium azide in DMF as described in Example 1, gave the tetrazolyl derivative as a white crystalline solid. It had m.p. (EtOH) 249°–251° C Found; C, 63.35; H, 3.71; N, 19.66; $C_{15}H_{10}N_4O_2$; requires; C, 64.74; H, 3.62; N, 20.13%).

EXAMPLE 9

4-Ethyl-3-(tetrazol-5-yl) coumarin

By a similar procedure to that described in Example 1, 3-cyano-4-ethyl coumarin was converted to its tetrazolyl derivative, m.p. (EtOH) 210°–212° C (Found; C, 59.33; H, 4.29; N, 23.25; $C_{12}H_{10}N_4O_2$ requires; C, 59.50; H, 4.16; N, 23.12%).

EXAMPLE 10

4-n-Propyl-3-(tetrazol-5-yl) coumarin

The reaction of 3-cyano-4-n-propyl coumarin (41.67 g; 0.196 mole) with ammonium azide as described in Example 1 afforded the title product, m.p. (EtOH) 178°–181° C (Found; C, 61.03; H, 4.95; N, 22.48; $C_{13}H_{12}N_4O_2$ requires; C, 60.93; H, 4.72; N, 21.86%).

EXAMPLE 11

4-Phenyl-3-(tetrazol-5-yl) coumarin

In a similar manner to that described in Example 1, 3-cyano-4-phenyl coumarin (12 g; 0.049 mole) was converted to its tetrazolyl derivative, m.p. (EtOH) 230°–232° C (d). (Found; C, 66.06; H, 3.74; N, 19.53; $C_{16}H_{10}N_4O_2$ requires; C, 66.20; H, 3.47; N, 19.30%).

EXAMPLE 12 a. 3-Cyano-6,7-diethyl-4-methyl coumarin

A mixture of 4,5-diethyl-2-hydroxy acetophenone (29g; 0.151 mole) and ethyl cyanoacetate (24ml) was added to a solution of sodium (0.70g) in ethanol (200ml) and the mixture stood for 1hr. at room temperature. After then refluxing for 3hrs. the mixture was cooled and the white crystalline precipitate filtered off. Recrystallisation from ethanol afforded material of m.p. 169° C. (Found; C, 74.53, H, 6.37; N, 5.81; $C_{15}H_{15}NO_2$ requires; C, 74.67; H, 6.27; N, 5.80%).

b. 6,7-Diethyl-4-methyl-3(tetrazol-5-yl) coumarin

Using the procedure outlined in example 5, 3-cyano-6,7-diethyl-4-methyl coumarin (17g; 0.07 mole) was converted into its tetrazolyl derivative, m.p. (EtOH) 202°–204° C. (Found; C, 63.28; H, 5.97; N, 19.56; $C_{15}H_{16}N_4O_2$ requires; C, 63.34; H, 5.67; N, 19.71%)

Biological Results

All of the coumarins prepared in the preceeding Examples were submitted for biological testing. The test system was the Rat Passive Cutaneous Anaphylaxis (PCA) test described below in (ii)

i. Serum containing heat labile homocytotropic antibody was raised in rats by a method similar to that used by Mota. (I. Mota Immunology 1964, 7,681).

Male Wistar rats of 250–300 g, were injected intraperitoneally with 0.5 of Bordatella pertussis vaccine (containing 4 × $10^{10}$ dead organism per ml.) and subcutaneously with 0.5 ml of an emulsion of adjuvant. Rats were bled by cardiac puncture on day 18, the blood was pooled and separated and serum stored at −20° and thawed only once before use.

ii. The P.C.A. test was similar to that described by Ovary and Bier (A. Ovary and O. E. Bier, Proc.Soc. Exp. Biol.Med. 1952, 81, 584) and Goose and Blair (J. Goose and AMJ. N. Blair, Immunology 1969, 16, 769).

0.1 ml of each of six twofold serial dilutions of the serum in 0.9% saline were injected intradermally into separate sites on the shaved dorsal surface of 250–350 g. Wistar rats. 72 hours later the animals were challenged by i.v. injection of 0.3 ml of 1% ovalbumin mixed with 0.1 ml of a 5% solution of pontamine sky blue dye in isotonic saline buffered with pH. 7.2 Sorenson buffer (P.B.S.). The rats were killed after 20 minutes and the diameter of the blue wheals at the antibody injection sites were measured. The starting dilution of the serum was adjusted so that there was no response, after challenge, at the site of injection of the highest dilution and a maximum response at the lowest dilution. Typically, six twofold serial dilutions of the serum from 1/4 to 1/128 were used.

Compounds were tested for their ability to reduce the diameter of the wheals at the injection sites of dilutions of antibody which on all the controls have less than maximum response. Amounts of the compounds were administered to rats each amount to a test group of six animals at a specified time prior to intravenous challenge with ovalbumin. The diameters of the blue wheals which developed on the tests group of animals were compared with those on a control group of six animals treated in the same way as the test group, but which had not received the compound under test.

% Inhibition of P.C.A. = 100 (1 − a/b)

a = The mean of the sum of the diameters of the wheals produced in the test group of animals at those antibody sites where all the control group of animals gave less than maximum response.

b = The mean of the sum of diameters of the wheals produced in the control group of animals at those antibody sites where all the animals gave less than maximum response.

The preferred method of administration was a solution of the test compound dissolved in pH 7.2 buffer and neutralised with sodium bicarbonate.

| BIOLOGICAL RESULTS | DOSE (mg/kg) | TIME (mins) | % INHIBITION OF RAT PCA RESPONSE |
|---|---|---|---|
| Example 1 | | | |
| 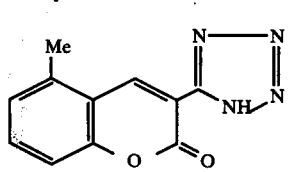 | 25 | 0 | 26 |
| | 100 | 0 | 46 |
| | 25 | 60 | 38 |
| | 100 | 60 | 48 |
| Example 2 | | | |
| 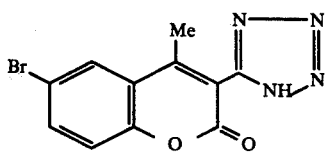 | 25 | 0 | 24 |
| | 100 | 0 | 43 |
| | 25 | 60 | 36 |
| | 100 | 60 | 44 |
| Example 3 | | | |
| 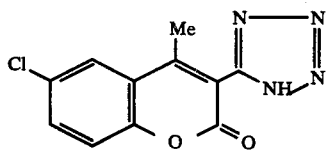 | 25 | 0 | 21 |
| | 100 | 0 | 27 |
| | 25 | 60 | 28 |
| | 100 | 60 | 35 |

-continued

| BIOLOGICAL RESULTS | DOSE (mg/kg) | TIME (mins) | % INHIBITION OF RAT PCA RESPONSE |
|---|---|---|---|
| Example 4 | | | |
| 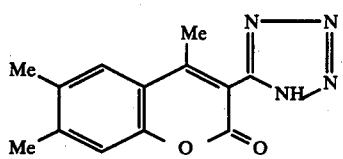 | 25<br>100<br>25<br>100 | 0<br>0<br>30<br>30 | 22<br>34<br>47<br>70 |
| Example 5 | | | |
| 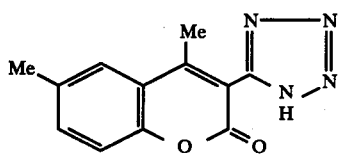 | 25<br>100<br>25<br>100 | 0<br>0<br>60<br>60 | 35<br>70<br>32<br>19 |
| Example 6 | | | |
| 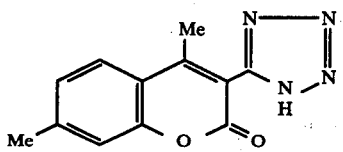 | 25<br>100<br>25<br>100 | 0<br>0<br>30<br>30 | 31<br>67<br>42<br>45 |
| Example 7 | | | |
| 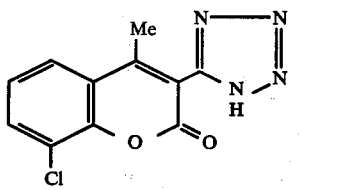 | 25<br>100<br>25<br>100 | 0<br>0<br>30<br>30 | 62<br>71<br>19<br>26 |
| Example 8 | | | |
| 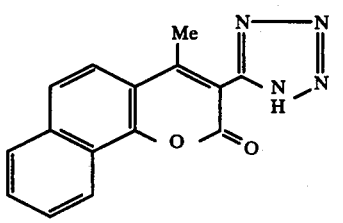 | 25<br>100<br>25<br>100 | 0<br>0<br>60<br>60 | 16<br>21<br>20<br>30 |
| Example 9 | | | |
| 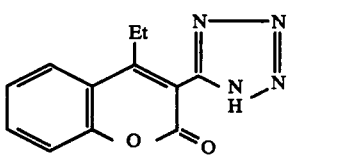 | 25<br>100<br>25<br>100 | 0<br>0<br>30<br>30 | 33<br>11<br>19<br>70 |
| Example 10 | | | |
| 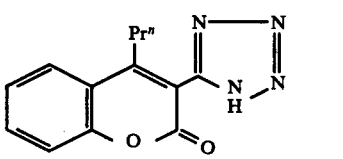 | 25<br>100<br>25<br>100 | 0<br>0<br>30<br>30 | −11<br>−1<br>−12<br>45 |

| BIOLOGICAL RESULTS (mg/kg) | DOSE (mins) | TIME RAT PCA RESPONSE | % INHIBITION OF |
|---|---|---|---|
| Example 11 | 25 | 0 | −12 |
| | 100 | 0 | − 2 |
| | 25 | 30 | −10 |
| | 100 | 30 | 14 |
| Example 12 | 25 | 10 | −6 |
| | 100 | 10 | −1 |
| | 25 | 60 | 10 |
| | 100 | 60 | 42 |

We claim:

1. A method for the prophylaxis of asthma, hay-fever and rhinitis in humans which comprises administering to a human in need thereof orally, parenterally or by insufflation a compound of the formula

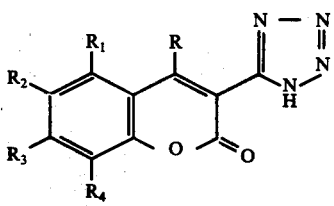

or a pharmaceutically acceptable salt thereof wherein R is lower alkyl, cyclopentyl, cyclohexyl, cycloheptyl or phenyl; $R_1$, is $R_2$, $R_3$ and $R_4$ are the same or different and each is hydrogen, lower alkyl, lower alkoxy, halogen, cyclohexyl, phenyl or benzyl; provided that when each of $R_1$, $R_2$, $R_3$ and $R_4$ is hydrogen, then R is not methyl, in an amount sufficient to be effective for the prophylaxis of asthma, hay-fever or rhinits, in combination with a pharmaceutically acceptable diluent or carrier suitable for said administration form.

2. A method according to claim 1 wherein R is lower alkyl.

3. A method according to claim 1 wherein R is methyl.

4. A method according to claim 1 wherein $R_4$ is halogen.

5. A method according to claim 1 wherein $R_2$ is lower alkyl.

6. A method according to claim 1 wherein $R_2$ and $R_3$ are both lower alkyl.

7. A method according to claim 1 wherein $R_3$ is lower alkoxy.

8. A method according to claim 1 wherein the compound is 6-bromo-4-methyl-3-(tetrazol-5-yl) coumarin.

9. A method according to claim 1 wherein R is lower alkyl, $R_2$ is lower alkyl, $R_3$ is lower alkoxy, or $R_2$ and $R_3$ are both lower alkyl and $R_4$ is halogen.

10. A method according to claim 1 wherein the compound is 3-(tetrazol-5-yl)-4,6,7-trimethyl coumarin.

11. A method according to claim 1 wherein the compound is 6-bromo-4-ethyl-3-(tetrzol-5-yl) coumarin.

12. A method according to claim 1 wherein the compound is 8-chloro-4-methyl-3-(tetrazol-5-yl) coumarin.

13. A method according to claim 1 wherein the compound is 4-ethyl-3-(tetrazol-5-yl) coumarin.

14. A method according to claim 1 wherein the compound is 4-methyl-8-nitro-3-(tetrazol-5-yl) coumarin.

15. A method according to claim 1 wherein the compound is 6-methoxy-4-methyl-3-(tetrazol-5-yl) coumarin.

16. A method according to claim 1 wherein the compound is 6,8-dichloro-4-methyl-3-(tetrazol-5-yl) coumarin.

17. A method according to claim 1 wherein the compound is 4,6,8-trimethyl-3-(tetrazol-5-yl) coumarin.

18. A method according to claim 1 wherein the compound is 4-n-propyl-3-(tetrazol-5-yl) coumarin.

19. A method according to claim 1 wherein the compound is 4,6-dimethyl-3-(tetrazol-5-yl) coumarin.

20. A method according to claim 1 wherein the compound is 4,7-dimethyl-3-(tetrazol-5-yl) coumarin.

21. A method according to claim 1 wherein the compound is 7,8-benzo-4-methyl-3-(tetrazol-5-yl) coumarin.

22. A method according to claim 1 wherein the compound is 4-phenyl-3-(tetrazol-5-yl) coumarin.

23. A method according to claim 1 wherein the compound is 6,7-diethyl-4-methyl-3-(tetrazol-5-yl) coumarin.

24. A method according to claim 1 wherein the compound is 4,6,7-trimethyl-3-(tetrazol-5-yl) coumarin.

25. A method according to claim 1 wherein the compound is 8-bromo-4-methyl-3-(tetrazol-5-yl) coumarin.

26. A method according to cliam 1 wherein the compound is 7-methoxy-4-methyl-3-(tetrazol-5-yl) coumarin.

27. A method according to claim 1 wherein the compound is 6-chloro-4-methyl-4-(tetrazol-5-yl) coumarin.

* * * * *